United States Patent [19]
Rudd

[11] 3,977,567
[45] Aug. 31, 1976

[54] INTRAVENOUS ALARM DEVICE
[76] Inventor: George H. Rudd, 1602 Post Oak, Irving, Tex. 75061
[22] Filed: Mar. 14, 1975
[21] Appl. No.: 558,230

[52] U.S. Cl. .................................. 222/39; 222/58; 128/214 E; 128/DIG. 13
[51] Int. Cl.² ........................................ G01F 15/00
[58] Field of Search ......... 128/214 E, 214 C, 214 F, 128/DIG. 13, 227; 222/39, 58; 116/109, 121

[56] References Cited
UNITED STATES PATENTS
2,469,230  5/1949  Harper .................................. 222/58
3,287,721  11/1966  Baehr ............................ 128/214 E Primary Examiner—Stanley H. Tollberg
Attorney, Agent, or Firm—Howard E. Moore; Gerald G. Crutsinger

[57] ABSTRACT

Apparatus for actuating an alarm to alert medical personnel that an intravenous fluid has been fully administered to the quantity ordered by the attending physician. A liquid dispensing container secured to one side of a balance arm with a counterweight secured to the other side of the balance arm opposite the fulcrum about which the balance arm is pivotally secured such that when balanced, a magnet on the balance arm actuates a switch, closing an electrical circuit to energize an alarm which alerts attending personnel. The fulcrum pin is secured to a support member which is secured to a support such as an IV stand.

8 Claims, 3 Drawing Figures

INTRAVENOUS ALARM DEVICE

BACKGROUND OF THE INVENTION

During the treatment of a patient who is ill, doctors often find it necessary to administer large dosages of fluid medications, solutions, and fluid supplements intravenously over extended periods of time commonly referred to as "IV's". These fluids and solutions include blood, glucose, dextrose, saline, and a wide variety of antibiotics and other drugs suspended in liquid which must be administered at a certain quantity per a period of time or continuously administered one bottle after another.

These fluids and solution medications are commonly administered intravenously into the body from 500 cc and 1,000 cc bottles.

Because of shortages in trained personnel in the hospitals it has become increasingly difficult to monitor each patient continuously to determine if the intravenous fluid has been fully administered to the doctor's orders.

Devices heretofore devised to alert nurses or other trained personnel when the IV solution is exhausted, have commonly involved the use of spring tension devices having large external forces which effect the accuracy of the device itself.

SUMMARY OF THE INVENTION

I have devised an intravenous alarm device which has reduced external forces to a minimum to thereby provide a more accurate indication of the amount of fluid which is passed from the IV bottle.

A liquid dispensing container such as an IV bottle is suspended from one side of a balance arm which is pivotally secured about a fulcrum pin. The other side of the balance arm has a counterweight secured thereto to balance the balance arm. A magnet is positioned about the upper part of the balance arm and arranged to actuate a magnetically actuated switch when the balance arm is in equilibrium which will close the circuit to actuate an alarm to signal attending personnel.

The balance arm is pivotally secured by the fulcrum pin to a support member having downwardly extending spaced apart legs. The support member is secured to a support arm such as an IV stand.

The counterweight is moveably secured to the counterweight side of the balance arm by means such as a hook suspended from graduated apertures formed in the balance arm. The device is initially balanced by suspending full IV bottle from the load side of the balance arm and placing the counterweight in the extreme outer hole from the fulcrum pin and adjusting a sliding counterweight provided to compensate for the weight of the container until the device is balanced and actuates the alarm. Upon balancing the device the counterweight is then removed and moved inwardly to the aperture corresponding with the number of cc's to be administered to the patient whereupon the load side containing the IV bottle will move downwardly and the counterweight side will move upwardly unbalancing the balance arm and causing the alarm device to become unactuated. As fluid is dispensed from the IV bottle into the patient, the IV bottle will become lighter whereupon the load side of the balance arm will move upwardly and the counterweight side downwardly pivoting about the fulcrum pin. When the predetermined amount of liquid is dispensed from the IV bottle, the balance arm will become rebalanced actuating the alarm device to alert attending personnel.

A primary object of the invention is to provide a more accurate alarm device in which external forces are reduced to a minimum since said external forces would reduce the accuracy of the result.

Another object of the invention is to provide an alarm system which requires minimum time to set up.

Another object of the invention is to provide an alarm system which is variable as to weight of liquid to be dispensed since the doctors do not always prescribe a full bottle of intravenous liquid to be injected.

Another object of the invention is to provide an alarm device which may alert trained personnel as to the progress of the patient's intravenous medication.

Other and further objects of the invention will become apparent upon referring to the detailed description hereinafter following and to the drawings annexed hereto.

BRIEF DESCRIPTION OF DRAWINGS

Drawings of a preferred embodiment of the invention are annexed hereto so that the invention may be better and more fully understood, in which.

Numeral references are employed to designate like parts in the drawing and like numerals indicate like parts throughout the various figures of the drawings.

DESCRIPTION OF A PREFERRED EMBODIMENT

Figure 2:
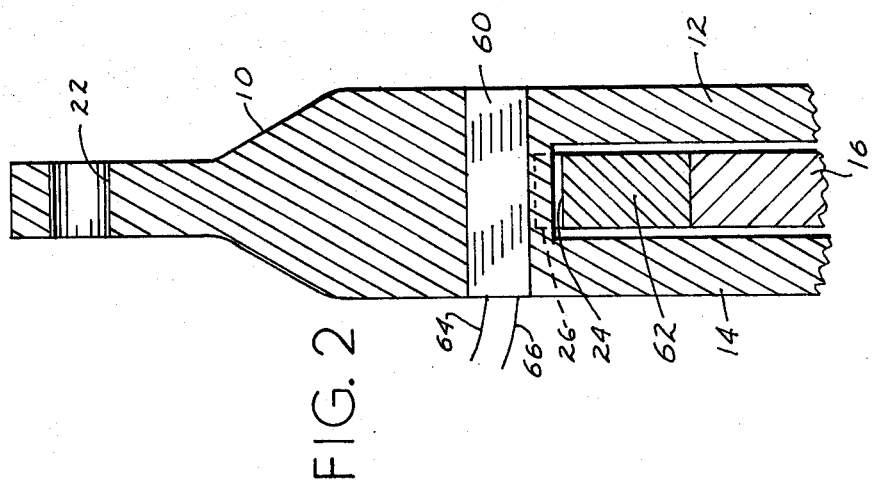
FIG. 2 is a cross-sectional view taken along line 2—2 of FIG. 1.
Figure 3:
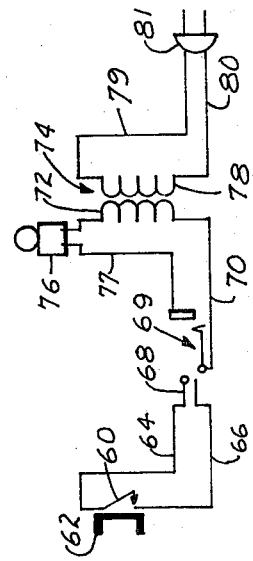
FIG. 3 is a diagrammatic view of the electrical circuit for the alarm system.
Figure 1:
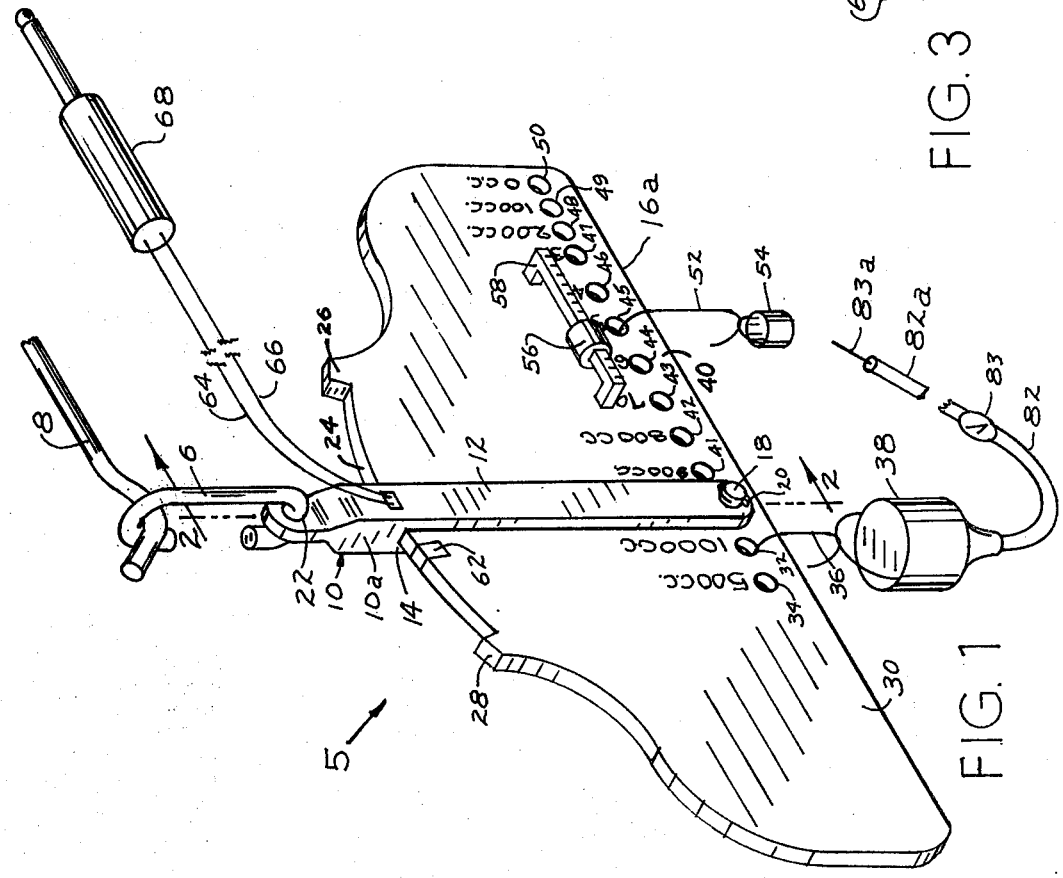
FIG. 1 is a front perspective view of the IV alarm.

The IV alarm 5 generally comprises a support member 10 having downwardly extending spaced legs 12 and 14, and a balance arm 16 pivotally secured between the legs 12 and 14 and by means of fulcrum pin 18 journalled through the lower end of legs 12 and 14 in the center of the lower edge 16a of balance arm 16. The fulcrum pin 18 is pivotally secured by cotter pin 20. The support member 10 has aperture 22 therein through which connector 6 is slideably disposed securing the device to support arm 8.

Balance arm 16 has an upper edge 24 which is slightly curved to allow rotative movement between the legs 12 and 14 of support member 10. Pivotal movement of balance arm 16 is limited by lugs 26 and 28 extending upwardly at each end of the upper edge 24 and are arranged to engage support member 10.

Means to secure a liquid dispensing container such as IV bottle 38 comprise spaced apertures 32 and 34 formed in load side 30 of balance arm 16 to accept hook 36 from which IV bottle 38 is suspended. The IV bottle 38 may contain various liquids such as blood, dextrose, saline solution, antibiotic solutions, etc. which may be fed into the body intravenously through tube 82 and needle 83a. The IV bottle 38 may be constructed of glass as illustrated or may be a plastic bag or other container as is now often used in hospitals.

The IV bottle 38 is suspended above the patient such that the liquid is drawn from the bottle 38 by gravity. The fluid is drawn into tube 82 which is secured to the lower end of the IV bottle 38 and through a valve 83 where the rate of flow may be adjusted to the doctor's perscription. The valve 83 is connected to a tube 82a which has a needle 83a secured thereto. The needle is placed in the vein of the patient, usually in the arm, and the fluid thus passes into the body.

Means moveably securing counterweight 54 to counterweight side 40 of balance arm 16 on the opposite side of fulcrum pin 18 from the liquid dispensing container comprises apertures 41, 42, 43, 44, 45, 46, 47, 48, 49, and 50 formed in the lower edge 16a of balance arm 16 to accept the suspension hook 52 for counterweight 54. As illustrated in the preferred embodiment apertures 41–50 have indicia corresponding to the number of cc's to be dispensed from 900 cc's to 0 cc's, respectively.

A sliding counterweight 56, slideably disposed on slide bar 58, is secured to counterweight side 40 to offset the weight of the empty IV bottle 38 and other minor inconsistencies in the weight of the structure.

An actuating means such as magnet 62 is positioned in upper edge 24 of the balance arm 16 such that when the balance arm is balanced the magnet energizes actuated means such as magnetically actuated switch 60 positioned in end 10a of support member 10 adjacent the upper edge 24 of balance arm 16. The magnetically actuated switch 60 has leads 64 and 66 connected to the contacts of switch 60. A plug 68 and jack 69 are illustrated in the preferred embodiment so that the alarm device 5 may be portable and moved from room to room. Lead 66 is secured through one side of plug 68 and jack 69 to a lead 70 which is secured to one side of secondary coil 72 of transformer 74. The other side of secondary coil 74 is connected to a signal means such as an alarm 76 which may be a bell, buzzer, or light. Lead 77 connects the other side of the alarm to wire 64 through the other side of plug 68 and jack 69. A complete circuit is formed when switch 60 is actuated by magnet 62. The primary coil 78 of transformer 74 has leads 79 and 80 which are connected to a power source by means of plug 81.

In a relationship where L equals the distance between the fulcrum pin 18 and aperture 32, W equals the weight of the fluid in IV bottle 38, $l$ equals the distance between the fulcrum pin 18 and aperture 41 and $l$ also equals the distance between each of spaced apertures 41–50, and $w$ equals the weight of counterweight 54; then $L \times W$ must equal $l \times w$ to balance the balance arm 16. It should be readily apparent that when the condition exists where $L \times W$ is slightly less than $l \times w$, the counterweight side 40 of balance arm 16 moves downwardly positioning magnet 62 under magnetically operated switch 60 to close the contacts of switch 60, completing a circuit to actuate alarm 76.

The balance arm 16 is arranged to be balanced at the outset with a full IV botle 38 suspended from aperture 32 or 34 and counterweight 54 is suspended from the outer aperture 50, such that $L \times W = l \times w$. The counterweight 54 is then moved to the left of aperture 50 to one of apertures 41–49 corresponding to the amount of liquid to be dispensed from the IV bottle 38, each aperture representing 100cc of the liquid. When the predetermined weight of liquid has been dispensed from the IV bottle 38, the condition will be such $L \times W = l \times w$, thus tilting the balance arm 16 such that the magnet 62 will actuate switch 60 actuating the alarm 76.

A typical example would be a 1,000 cc IV bottle 38 suspended from aperture 32 one unit of length from the fulcrum pin 18. The counterweight 54 which weighs the same as 100 cc of fluid in the IV bottle 38 would be suspended from aperture 50 ten units of length on the opposite side of the fulcrum pin 18. Applying the previously discussed formula, $1,000 (1) = 100 (10)$, and the balance arm 16 would be an equilibrium.

To dispense 400 cc's of liquid from IV bottle 38, the counterweight 54 is moved inwardly four units of length $l$ to aperture 46 having indicia 400 cc's corresponding therewith. The balance arm 16 will no longer be in equilibrium since $1,000 (1)$ is less than $100 (10 - 4)$ and the load side 30 of balance arm 16 would be in a lower position. The IV bottle 38 is then regulated to dispense the liquid therefrom. As the liquid is dispensed, the weight of the IV bottle 38 will be reduced at a rate of approximately 1 gram per 1 cu. cm. The load side 30 of the balance arm 16 will move upwardly as the liquid is dispensed therefrom. When 400 cc's of liquid has been dispensed from the IV bottle 38, then the formula will be $1,000 - 400 (1) = 100 \times (10 - 4)$ or $600 (1) = 100 (6)$ and the balance arm 16 will be in equilibrium once more and magnet 62 is positioned under magnetically actuated switch 60 to actuate the alarm 76.

It should be readily apparent that a 500 cc IV bottle 38 would be suspended from aperture 34, two units of length from fulcrum pin 18. The formula would be $500 (2) = 100 (10)$ and the procedure would be the same except counterweight 54 would be moved inwardly by twice the number of apertures corresponding to the amount of fluid to be dispensed.

Operation of the hereinbefore described device is as follows:

The IV alarm 5 is suspended from a support arm 8 and an IV bottle 38 containing a predetermined amount of liquid such as 500 or 1,000 cc's is secured in the appropriate aperture 32 or 34 corresponding to the weight of IV bottles 38 contents. The counterweight 54 is initially placed in aperture 50 with indicia 0 cc's. The sliding counterweight 56 is then adjusted along slide bar 58 to balance the balance arm 16 until alarm 76 is energized. After balancing the balance arm 16 the counterweight 54 is moved from aperture 50, in which the counterweight 54 is first suspended, inwardly toward the fulcrum pin 18 the number of apertures corresponding to the predetermined volume of liquid to be injected into the patient. If the full IV bottle 38 is to be administered the counterweight 54 is completely removed after initial balancing. The device, after moving counterweight 54, is thus unbalanced with the IV bottle 38 suspended in aperture 32 or 34 pivoting the load side of balance arm 16 downwardly and counterweight side 40 upwardly about the fulcrum pin 18. The IV bottle 38 is then secured in communication with the patient by tube 82 and needle 83a which is placed in a vein and the desired rate of flow into the patient is adjusted by valve 83. The liquid from IV bottle 38 then begins to flow into the patient's vein until the desired amount of liquid has been drained from the IV bottle 38. As the liquid from IV bottle 38 is dispensed the bottle becomes lighter and load side 30 of balance arm 16 will begin to rise thus returning to the balanced position, as the IV bottle 38 nears the predetermined volume of liquid to be dispensed. The balance arm 16 upon becoming rebalanced will align magnet 62 under magnetically actuated switch 60, closing the contact switch 60, thereby completing a circuit to actuate the alarm 76. It should be apparent that the alarm 76 may be located in the remote position so that one person may be assigned to monitor all the intravenous solutions being administered to the various patients, thereby reducing the time needed to check the IV injections, and reducing the chances of accidents occurring.

It should be appreciated that this device may be used to alert personnel when the full amount of IV solution has been administered to the patient as per doctor's orders and also to check the rate at which the IV fluid is being administered. For example, if a doctor's order is for a predetermined volume to be administered in a certain amount of time, the device can be used to alert personnel that the prescribed volume of fluid for the prescribed time has been administered.

From the foregoing it should be readily apparent that the embodiment hereinbefore described accomplishes the objects of the invention hereinbefore set forth. It should be appreciated that other and further embodiments of the invention may be devised without departing from the basic concept thereof.

Having described my invention, I claim:

1. An alarm device to alert that a predetermined amount of liquid has been dispensed from a liquid dispensing container comprising: a balance arm; a support member; pivot means pivotally securing the balance arm to the support member; a counterweight, means to movably secure the counterweight to the balance arm on one side of the pivot means; means to secure a liquid dispensing container to the balance arm on the other side of the pivot means, said counterweight being selectively positionable to initiate pivotal movement of said balance arm upon dispensing a predetermined amount of liquid from a liquid dispensing container secured to the balance arm; alarm means actuated by pivotal movement of the balance arm in response to dispensing of a predetermined amount of liquid from the container; and legs on the support member embracing the balance arm with the lower end of said legs being pivotally attached to the lower side of the balance arm, the upper side of the balance arm being arcuately shaped and extending between said legs.

2. The combination called for in claim 1 with the addition of spaced stop members on the upper side of the balance arm arranged to contact the support member to limit the pivotal movement of the balance arm.

3. In an intravenous injection alarm device: a support member having an attachment leg thereon; a balance arm; pivot means to pivotally attach the balance arm to the leg adjacent the lower edge of the balance arm; spaced lugs attached to the balance arm on opposite sides of the support member arranged to engage the support member to limit pivotal movement of the balance arm; first engagement means on the balance arm on one side of the pivot means; second engagement means on the balance arm on the other side of said pivot means; a liquid dispensing container arranged to be suspended from the first engagement means; a counterweight arranged to selectively engage the second engagement means, said counterweight being arranged to be moved along the second engagement means depending upon the amount of liquid to be dispensed from the container; and a signal means arranged to be actuated by the pivotal movement of the balance arm to indicate when a predetermined amount of liquid has been dispensed from the container.

4. In an intravenous injection alarm device: a support member having an attachment leg thereon; a balance arm pivotally secured to the leg; pivot means to pivotally attach the balance arm to the leg adjacent the lower edge of the balance arm; first engagement means on the balance arm on one side of the pivot means; second engagement means spaced along the balance arm on the other side of the pivot means; a liquid dispensing container arranged to be suspended from the first engagement means; a counterweight arranged to selectively engage the spaced second engagement means to balance the balance arm depending upon the amount of liquid in the container, said counterweight being arranged to be selectively moved along the spaced second engagement means depending upon the amount of liquid to be dispensed from the container; and signal means arranged to be actuated by pivotal movement of the balance arm to indicate when a predetermined amount of liquid has been dispensed from the container, said signal means including a magnet on the balance arm and a magnetic switch on the support member whereby when the balance arm is pivoted to bring the magnet into juxtaposition to the magnetic switch, the switch will be closed to actuate an alarm.

5. In an intravenous injection alarm device: a support member having an attachment leg thereon; a balance arm; pivot means to pivotally attach the balance arm to the leg adjacent the lower edge of the balance arm; first engagement means on the balance arm on one side of the pivot means; second engagement means spaced along the balance arm on the other side of pivot means; a liquid dispensing container arranged to be suspended from the first engagement means; a first counterweight arranged to selectively engage the spaced second engagement means to balance the balance arm depending upon the amount of liquid in the container, said first counterweight being arranged to be selectively moved along the spaced engagement means depending upon the amount of liquid to be dispensed from the container; a second counterweight slidably secured to the side of the balance arm whereon is located the second engagement means; and signal means arranged to be actuated by pivotal movement of the balance arm to indicate when a predetermined amount of liquid has been dispensed from the container.

6. In an intravenous injection alarm device: a support member having an attachment leg thereon; a balance arm; pivot means pivotally securing the balance arm to the leg adjacent the lower edge of the balance arm, said balance arm having at least one first aperture formed in one side of the balance arm outwardly of the pivot means and having a plurality of spaced second apertures formed in the other side of the balance arm and spaced outwardly thereon from the other side of the pivot means; indicia adjacent said spaced second apertures to indicate the selective amount of liquid to be dispensed from a container; a liquid dispensing container arranged to be suspended from the first aperture; a counterweight arranged to be selectively engaged to the spaced second apertures to balance the balance arm depending upon the amount of liquid in the container, said counterweight being arranged to be selectively moved along the spaced second apertures depending upon the amount of liquid to be dispensed from the container; and signal means arranged to be actuated by the pivotal movement of the balance arm to indicate when a predetermined amount of liquid has been dispensed from the container.

7. In a monitor device for liquid dispensing apparatus: a support member; a balance arm; pivot means securing said balance arm to said support member; means to secure a liquid dispensing container to the balance arm on a first side of said pivot means; a first counterweight; first connector means movably securing said first counterweight to said balance arm on a second side of said pivot means; a second counterweight; second connector means movably securing said second counterweight to said balance arm, said first and second counterweights being movable along said balance arm to establish a first position of said balance arm when a liquid dispensing container liquid is secured to said balance arm, said second counterweight being movable along said arm to cause said balance arm to move from said first position to a second position to establish the amount of liquid to be dispensed from said liquid dispensing container and causing said arm to return to said first position when the predetermined amount of liquid has been dispensed; and signal means arranged to be actuated by movement of the balance arm to said first position.

8. A process of monitoring the dispensing of material from a container comprising the steps of: pivotally supporting a balance arm; securing a container to the balance arm; positioning first and second counterweights on the balance arm to move the balance arm to a first position; moving one of the counterweights along said balance arm to create a controlled imbalance of the balance arm such that when a predetermined amount of material has been dispensed from the container the balance arm will be returned to the first position; dispensing material from the container; and generating a signal in response to movement of the balance arm to said first position.

* * * * *